(12) United States Patent
Walke et al.

(10) Patent No.: US 6,692,947 B2
(45) Date of Patent: Feb. 17, 2004

(54) HUMAN TRANSFERASE PROTEINS AND POLYNUCLEOTIDES ENCODING THE SAME

(75) Inventors: D. Wade Walke, Spring, TX (US); C. Alexander Turner, Jr., The Woodlands, TX (US); Glenn Friedrich, Houston, TX (US); Alejandro Abuin, The Woodlands, TX (US); Brian Zambrowicz, The Woodlands, TX (US); Arthur T. Sands, The Woodlands, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 88 days.

(21) Appl. No.: 09/734,492

(22) Filed: Dec. 11, 2000

(65) Prior Publication Data

US 2003/0166839 A1 Sep. 4, 2003

Related U.S. Application Data

(60) Provisional application No. 60/170,408, filed on Dec. 13, 1999.

(51) Int. Cl.$^7$ .............. C07H 21/04; C12N 1/20; C12N 15/63; C12N 9/10

(52) U.S. Cl. .............. 435/193; 435/320.1; 435/252.3; 435/252.33; 435/348; 435/419; 435/325; 536/23.2

(58) Field of Search ............... 536/23.2; 435/193, 435/252.3, 252.33, 348, 419, 325, 320.1

(56) References Cited

PUBLICATIONS

Cabuy et al *Homo sapiens* beta–4–N– acetylgalactosaminyltransferase mRNA, complete cds. NCBI gi|21105713|gb|AF510036.1|[21105713] May 23, 2002. Alignment with SEQ ID No.: 1.*

* cited by examiner

*Primary Examiner*—Rebecca E. Prouty
*Assistant Examiner*—Sheridan L. Swope

(57) ABSTRACT

Novel human polynucleotide and polypeptide sequences are disclosed that can be used in therapeutic, diagnostic, and pharmacogenomic applications.

5 Claims, No Drawings

SEQUENCE LISTING

<160> NUMBER OF SEQ ID NOS: 37

<210> SEQ ID NO 1
<211> LENGTH: 1521
<212> TYPE: DNA
<213> ORGANISM: Homo sapiens

<400> SEQUENCE: 1

| | | | | | |
|---|---|---|---|---|---|
| atgacttcgg | gcggctcgag | atttctgtgg | ctcctcaaga | tattggtcat | aatcctggta | 60 |
| cttggcattg | ttggatttat | gttcggaagc | atgttccttc | aagcagtgtt | cagcagcccc | 120 |
| aagccagaac | tcccaagtcc | tgccccgggt | gtccagaagc | tgaagcttct | gcctgaggaa | 180 |
| cgtctcagga | acctctttc | ctacgatgga | atctggctgt | cccgaaaaa | tcagtgcaaa | 240 |
| tgtgaagcca | acaaagagca | gggaggttac | aactttcagg | atgcctatgg | ccagagcgac | 300 |
| ctcccagcgg | tgaaagcgag | gagacaggct | gaatttgaac | actttcagag | gagagaaggg | 360 |
| ctgccccgcc | cactgcccct | gctggtccag | cccaacctcc | cctttgggta | cccagtccac | 420 |
| ggagtggagg | tgatgcccct | gcacacggtt | cccatcccag | gcctccagtt | tgaaggaccc | 480 |
| gatgccccg | tctatgaggt | caccctgaca | gcttctctgg | ggacactgaa | caccccttgct | 540 |
| gatgtcccag | acagtgtggt | gcagggcaga | ggccagaagc | agctgatcat | ttctaccagt | 600 |
| gaccggaagc | tgttgaagtt | cattcttcag | cacgtgacat | acaccagcac | ggggtaccag | 660 |
| caccagaagg | tagacatagt | gagtctggag | tccaggtcct | cagtggccaa | gtttccagtg | 720 |
| accatccgcc | atcctgtcat | acccaagcta | tacgaccctg | gaccagagag | gaagctcaga | 780 |
| aacctggtta | ccattgctac | caagactttc | ctccgccccc | acaagctcat | gatcatgctc | 840 |
| cggagtattc | gagagtatta | cccagacttg | accgtaatag | tggctgatga | cagccagaag | 900 |
| cccctggaaa | ttaaagacaa | ccacgtggag | tattacacta | tgccctttgg | gaagggttgg | 960 |
| tttgctggta | ggaacctggc | catatctcag | gtcaccacca | aatacgttct | ctgggtggac | 1020 |
| gatgattttc | tcttcaacga | ggagaccaag | attgaggtgc | tggtggatgt | cctggagaaa | 1080 |
| acagaactgg | acgtggtagg | cggcagtgtg | ctgggaaatg | tgttccagtt | taagttgttg | 1140 |
| ctggaacaga | gtgagaatgg | ggcctgcctt | cacaagagga | tgggatttt | ccaacccctg | 1200 |
| gatggcttcc | ccagctgcgt | ggtgaccagt | ggcgtggtca | acttcttcct | ggcccacacg | 1260 |
| gagcgactcc | aaagagttgg | ctttgatccc | gcctgcaac | gagtggctca | ctcagaattc | 1320 |
| ttcattgatg | ggctagggac | cctactcgtg | gggtcatgcc | cagaagtgat | tataggtcac | 1380 |
| cagtctcggt | ctccagtggt | ggactcagaa | ctggctgccc | tagagaagac | ctacaataca | 1440 |
| taccggtcca | acaccctcac | ccgggtccag | ttcaagctgg | cccttcacta | cttcaagaac | 1500 |
| catctccaat | gtgccgcata | a | | | | 1521 |

<210> SEQ ID NO 2
<211> LENGTH: 506
<212> TYPE: PRT
<213> ORGANISM: Homo sapiens

<400> SEQUENCE: 2

Met Thr Ser Gly Gly Ser Arg Phe Leu Trp Leu Leu Lys Ile Leu Val
 1               5                  10                  15

Ile Ile Leu Val Leu Gly Ile Val Gly Phe Met Phe Gly Ser Met Phe
            20                  25                  30

Leu Gln Ala Val Phe Ser Ser Pro Lys Pro Glu Leu Pro Ser Pro Ala

-continued

```
              35                  40                  45
Pro Gly Val Gln Lys Leu Lys Leu Leu Pro Glu Glu Arg Leu Arg Asn
             50                  55                  60
Leu Phe Ser Tyr Asp Gly Ile Trp Leu Phe Pro Lys Asn Gln Cys Lys
 65                  70                  75                  80
Cys Glu Ala Asn Lys Glu Gln Gly Gly Tyr Asn Phe Gln Asp Ala Tyr
                     85                  90                  95
Gly Gln Ser Asp Leu Pro Ala Val Lys Ala Arg Arg Gln Ala Glu Phe
                100                 105                 110
Glu His Phe Gln Arg Arg Glu Gly Leu Pro Arg Pro Leu Pro Leu Leu
                115                 120                 125
Val Gln Pro Asn Leu Pro Phe Gly Tyr Pro Val His Gly Val Glu Val
            130                 135                 140
Met Pro Leu His Thr Val Pro Ile Pro Gly Leu Gln Phe Glu Gly Pro
145                 150                 155                 160
Asp Ala Pro Val Tyr Glu Val Thr Leu Thr Ala Ser Leu Gly Thr Leu
                    165                 170                 175
Asn Thr Leu Ala Asp Val Pro Asp Ser Val Val Gln Gly Arg Gly Gln
                180                 185                 190
Lys Gln Leu Ile Ile Ser Thr Ser Asp Arg Lys Leu Leu Lys Phe Ile
                195                 200                 205
Leu Gln His Val Thr Tyr Thr Ser Thr Gly Tyr Gln His Gln Lys Val
            210                 215                 220
Asp Ile Val Ser Leu Glu Ser Arg Ser Ser Val Ala Lys Phe Pro Val
225                 230                 235                 240
Thr Ile Arg His Pro Val Ile Pro Lys Leu Tyr Asp Pro Gly Pro Glu
                    245                 250                 255
Arg Lys Leu Arg Asn Leu Val Thr Ile Ala Thr Lys Thr Phe Leu Arg
                260                 265                 270
Pro His Lys Leu Met Ile Met Leu Arg Ser Ile Arg Glu Tyr Tyr Pro
                275                 280                 285
Asp Leu Thr Val Ile Val Ala Asp Asp Ser Gln Lys Pro Leu Glu Ile
            290                 295                 300
Lys Asp Asn His Val Glu Tyr Tyr Thr Met Pro Phe Gly Lys Gly Trp
305                 310                 315                 320
Phe Ala Gly Arg Asn Leu Ala Ile Ser Gln Val Thr Thr Lys Tyr Val
                    325                 330                 335
Leu Trp Val Asp Asp Asp Phe Leu Phe Asn Glu Glu Thr Lys Ile Glu
                340                 345                 350
Val Leu Val Asp Val Leu Glu Lys Thr Glu Leu Asp Val Val Gly Gly
                355                 360                 365
Ser Val Leu Gly Asn Val Phe Gln Phe Lys Leu Leu Leu Glu Gln Ser
            370                 375                 380
Glu Asn Gly Ala Cys Leu His Lys Arg Met Gly Phe Gln Pro Leu
385                 390                 395                 400
Asp Gly Phe Pro Ser Cys Val Val Thr Ser Gly Val Val Asn Phe Phe
                    405                 410                 415
Leu Ala His Thr Glu Arg Leu Gln Arg Val Gly Phe Asp Pro Arg Leu
                420                 425                 430
Gln Arg Val Ala His Ser Glu Phe Phe Ile Asp Gly Leu Gly Thr Leu
                435                 440                 445
Leu Val Gly Ser Cys Pro Glu Val Ile Ile Gly His Gln Ser Arg Ser
            450                 455                 460
```

Pro Val Val Asp Ser Glu Leu Ala Ala Leu Glu Lys Thr Tyr Asn Thr
465                 470                 475                 480

Tyr Arg Ser Asn Thr Leu Thr Arg Val Gln Phe Lys Leu Ala Leu His
            485                 490                 495

Tyr Phe Lys Asn His Leu Gln Cys Ala Ala
        500                 505

<210> SEQ ID NO 3
<211> LENGTH: 399
<212> TYPE: DNA
<213> ORGANISM: Homo sapiens

<400> SEQUENCE: 3
atggggagcg ctggcttttc cgtgggaaaa ttccacgtgg aggtggcctc tcgcggccgg      60
gaatgtgtct cggggacgcc cgagtgtggg aatcggctcg ggagtgcggg cttcggggat     120
ctctgcttgg aactcagagg cgctgaccca gcctggggcc cgtttgctgc ccacggggag     180
agccgccgtc agggctcgag atttctgtgg ctcctcaaga tattggtcat aatcctggta     240
cttggcattg ttggatttat gttcggaagc atgttccttc aagcagtgtt cagcagcccc     300
aagccagaac tcccaagtcc tgccccgggt gtccagaagc tgaagcttct gcctgaggaa     360
cgtctcagga acctctttc ctacgatgga atctggtga                            399

<210> SEQ ID NO 4
<211> LENGTH: 132
<212> TYPE: PRT
<213> ORGANISM: Homo sapiens

<400> SEQUENCE: 4

Met Gly Ser Ala Gly Phe Ser Val Gly Lys Phe His Val Glu Val Ala
1               5                   10                  15

Ser Arg Gly Arg Glu Cys Val Ser Gly Thr Pro Glu Cys Gly Asn Arg
            20                  25                  30

Leu Gly Ser Ala Gly Phe Gly Asp Leu Cys Leu Glu Leu Arg Gly Ala
        35                  40                  45

Asp Pro Ala Trp Gly Pro Phe Ala Ala His Gly Arg Ser Arg Arg Gln
    50                  55                  60

Gly Ser Arg Phe Leu Trp Leu Leu Lys Ile Leu Val Ile Ile Leu Val
65                  70                  75                  80

Leu Gly Ile Val Gly Phe Met Phe Gly Ser Met Phe Leu Gln Ala Val
                85                  90                  95

Phe Ser Ser Pro Lys Pro Glu Leu Pro Ser Pro Ala Pro Gly Val Gln
            100                 105                 110

Lys Leu Lys Leu Leu Pro Glu Glu Arg Leu Arg Asn Leu Phe Ser Tyr
        115                 120                 125

Asp Gly Ile Trp
    130

<210> SEQ ID NO 5
<211> LENGTH: 219
<212> TYPE: DNA
<213> ORGANISM: Homo sapiens

<400> SEQUENCE: 5
atgacttcgg gcggctcgag atttctgtgg ctcctcaaga tattggtcat aatcctggta      60
cttggcattg ttggatttat gttcggaagc atgttccttc aagcagtgtt cagcagcccc     120

```
aagccagaac tcccaagtcc tgccccgggt gtccagaagc tgaagcttct gcctgaggaa      180
cgtctcagga acctcttttc ctacgatgga atctggtga                             219
```

<210> SEQ ID NO 6
<211> LENGTH: 72
<212> TYPE: PRT
<213> ORGANISM: Homo sapiens

<400> SEQUENCE: 6

Met Thr Ser Gly Gly Ser Arg Phe Leu Trp Leu Leu Lys Ile Leu Val
1               5                   10                  15

Ile Ile Leu Val Leu Gly Ile Val Gly Phe Met Phe Gly Ser Met Phe
            20                  25                  30

Leu Gln Ala Val Phe Ser Ser Pro Lys Pro Glu Leu Pro Ser Pro Ala
        35                  40                  45

Pro Gly Val Gln Lys Leu Lys Leu Leu Pro Glu Arg Leu Arg Asn
    50                  55                  60

Leu Phe Ser Tyr Asp Gly Ile Trp
65                  70

<210> SEQ ID NO 7
<211> LENGTH: 555
<212> TYPE: DNA
<213> ORGANISM: Homo sapiens

<400> SEQUENCE: 7

```
atggggagcg ctggcttttc cgtgggaaaa ttccacgtgg aggtggcctc tcgcggccgg      60
gaatgtgtct cggggacgcc cgagtgtggg aatcggctcg ggagtgcggg cttcggggat     120
ctctgcttgg aactcagagg cgctgaccca gcctgggcc cgtttgctgc ccacggggagg    180 agccgccgtc agggctcgag atttctgtgg ctcctcaaga tattggtcat aatcctggta    240
cttggcattg ttggatttat gttcggaagc atgttccttc aagcagtgtt cagcagcccc    300
aagccagaac tcccaagtcc tgccccgggt gtccagaagc tgaagcttct gcctgaggaa    360
cgtctcagga acctcttttc ctacgatgga atctgtcctc ttgcttgttt caggctgttc    420
ccgaaaaatc agtgcaaatg tgaagccaac aaagagcagg gaggttacaa ctttcaggat   480
gcctatggcc agagcgacct cccagcggtg aaagcgagga gacaggctga atttgaacac    540
tttcagagga ggtaa                                                     555
```

<210> SEQ ID NO 8
<211> LENGTH: 184
<212> TYPE: PRT
<213> ORGANISM: Homo sapiens

<400> SEQUENCE: 8

Met Gly Ser Ala Gly Phe Ser Val Gly Lys Phe His Val Glu Val Ala
1               5                   10                  15

Ser Arg Gly Arg Glu Cys Val Ser Gly Thr Pro Glu Cys Gly Asn Arg
            20                  25                  30

Leu Gly Ser Ala Gly Phe Gly Asp Leu Cys Leu Glu Leu Arg Gly Ala
        35                  40                  45

Asp Pro Ala Trp Gly Pro Phe Ala Ala His Gly Arg Ser Arg Arg Gln
    50                  55                  60

Gly Ser Arg Phe Leu Trp Leu Leu Lys Ile Leu Val Ile Ile Leu Val
65                  70                  75                  80

Leu Gly Ile Val Gly Phe Met Phe Gly Ser Met Phe Leu Gln Ala Val

```
                       85                  90                  95
Phe Ser Ser Pro Lys Pro Glu Leu Pro Ser Pro Ala Pro Gly Val Gln
                  100                 105                 110

Lys Leu Lys Leu Leu Pro Glu Glu Arg Leu Arg Asn Leu Phe Ser Tyr
            115                 120                 125

Asp Gly Ile Cys Pro Leu Ala Cys Phe Arg Leu Phe Pro Lys Asn Gln
        130                 135                 140

Cys Lys Cys Glu Ala Asn Lys Glu Gln Gly Gly Tyr Asn Phe Gln Asp
145                 150                 155                 160

Ala Tyr Gly Gln Ser Asp Leu Pro Ala Val Lys Ala Arg Arg Gln Ala
                    165                 170                 175

Glu Phe Glu His Phe Gln Arg Arg
            180

<210> SEQ ID NO 9
<211> LENGTH: 372
<212> TYPE: DNA
<213> ORGANISM: Homo sapiens

<400> SEQUENCE: 9
atgacttcgg gcggctcgag atttctgtgg ctcctcaaga tattggtcat aatcctggta      60
cttggcattg ttggatttat gttcggaagc atgttccttc aagcagtgtt cagcagcccc     120
aagccagaac tcccaagtcc tgccccgggt gtccagaagc tgaagcttct gcctgaggaa     180
cgtctcagga acctcttttc ctacgatgga atctgtcctc ttgcttgttt caggctgttc     240
ccgaaaaatc agtgcaaatg tgaagccaac aaagagcagg gaggttacaa ctttcaggat     300
gcctatggcc agagcgacct cccagcggtg aaagcgagga cacaggctga atttgaacac     360
tttcagagga gg                                                         372

<210> SEQ ID NO 10
<211> LENGTH: 124
<212> TYPE: PRT
<213> ORGANISM: Homo sapiens

<400> SEQUENCE: 10

Met Thr Ser Gly Gly Ser Arg Phe Leu Trp Leu Leu Lys Ile Leu Val
1               5                  10                  15

Ile Ile Leu Val Leu Gly Ile Val Gly Phe Met Phe Gly Ser Met Phe
            20                  25                  30

Leu Gln Ala Val Phe Ser Ser Pro Lys Pro Glu Leu Pro Ser Pro Ala
        35                  40                  45

Pro Gly Val Gln Lys Leu Lys Leu Leu Pro Glu Glu Arg Leu Arg Asn
    50                  55                  60

Leu Phe Ser Tyr Asp Gly Ile Cys Pro Leu Ala Cys Phe Arg Leu Phe
65                  70                  75                  80

Pro Lys Asn Gln Cys Lys Cys Glu Ala Asn Lys Glu Gln Gly Gly Tyr
                85                  90                  95

Asn Phe Gln Asp Ala Tyr Gly Gln Ser Asp Leu Pro Ala Val Lys Ala
            100                 105                 110

Arg Arg Gln Ala Glu Phe Glu His Phe Gln Arg Arg
        115                 120

<210> SEQ ID NO 11
<211> LENGTH: 537
<212> TYPE: DNA
<213> ORGANISM: Homo sapiens
```

-continued

<400> SEQUENCE: 11

```
atgggagcg ctggctttc cgtgggaaaa ttccacgtgg aggtggcctc tcgcggccgg      60
gaatgtgtct cggggacgcc cgagtgtggg aatcggctcg ggagtgcggg cttcggggat   120
ctctgcttgg aactcagagg cgctgaccca gcctggggcc cgtttgctgc ccacgggagg   180
agccgccgtc agggctcgag atttctgtgg ctcctcaaga tattggtcat aatcctggta   240
cttggcattg ttggatttat gttcggaagc atgttccttc aagcagtgtt cagcagcccc   300
aagccagaac tcccaagtcc tgccccgggt gtccagaagc tgaagcttct gcctgaggaa   360
cgtctcagga acctctttc ctacgatgga atctggctgt cccgaaaaa tcagtgcaaa     420
tgtgaagcca acaaagagca gggaggttac aactttcagg atgcctatgg ccagagcgac   480
ctcccagcgg tgaaagcgag gagacaggct gaatttgaac actttcagag gaggtaa      537
```

<210> SEQ ID NO 12
<211> LENGTH: 182
<212> TYPE: PRT
<213> ORGANISM: Homo sapiens

<400> SEQUENCE: 12

```
Arg Arg Thr Asn Met Gly Ser Ala Gly Phe Ser Val Gly Lys Phe His
 1               5                  10                  15
Val Glu Val Ala Ser Arg Gly Arg Glu Cys Val Ser Gly Thr Pro Glu
             20                  25                  30
Cys Gly Asn Arg Leu Gly Ser Ala Gly Phe Gly Asp Leu Cys Leu Glu
         35                  40                  45
Leu Arg Gly Ala Asp Pro Ala Trp Gly Pro Phe Ala Ala His Gly Arg
     50                  55                  60
Ser Arg Arg Gln Gly Ser Arg Phe Leu Trp Leu Lys Ile Leu Val
65                  70                  75                  80
Ile Ile Leu Val Leu Gly Ile Val Gly Phe Met Phe Gly Ser Met Phe
                 85                  90                  95
Leu Gln Ala Val Phe Ser Ser Pro Lys Pro Glu Leu Pro Ser Pro Ala
            100                 105                 110
Pro Gly Val Gln Lys Leu Lys Leu Leu Pro Glu Glu Arg Leu Arg Asn
        115                 120                 125
Leu Phe Ser Tyr Asp Gly Ile Trp Leu Phe Pro Lys Asn Gln Cys Lys
    130                 135                 140
Cys Glu Ala Asn Lys Glu Gln Gly Gly Tyr Asn Phe Gln Asp Ala Tyr
145                 150                 155                 160
Gly Gln Ser Asp Leu Pro Ala Val Lys Ala Arg Arg Gln Ala Glu Phe
                165                 170                 175
Glu His Phe Gln Arg Arg
            180
```

<210> SEQ ID NO 13
<211> LENGTH: 357
<212> TYPE: DNA
<213> ORGANISM: Homo sapiens

<400> SEQUENCE: 13

```
atgacttcgg gcggctcgag atttctgtgg ctcctcaaga tattggtcat aatcctggta    60
cttggcattg ttggatttat gttcggaagc atgttccttc aagcagtgtt cagcagcccc   120
aagccagaac tcccaagtcc tgccccgggt gtccagaagc tgaagcttct gcctgaggaa   180
```

-continued

```
cgtctcagga acctcttttc ctacgatgga atctggctgt tcccgaaaaa tcagtgcaaa        240
tgtgaagcca acaaagagca gggaggttac aactttcagg atgcctatgg ccagagcgac        300
ctcccagcgg tgaaagcgag gagacaggct gaatttgaac actttcagag gaggtaa          357
```

<210> SEQ ID NO 14
<211> LENGTH: 118
<212> TYPE: PRT
<213> ORGANISM: Homo sapiens

<400> SEQUENCE: 14

```
Met Thr Ser Gly Gly Ser Arg Phe Leu Trp Leu Lys Ile Leu Val
 1               5                  10                  15

Ile Ile Leu Val Leu Gly Ile Val Gly Phe Met Phe Gly Ser Met Phe
                20                  25                  30

Leu Gln Ala Val Phe Ser Ser Pro Lys Pro Glu Leu Pro Ser Pro Ala
            35                  40                  45

Pro Gly Val Gln Lys Leu Lys Leu Leu Pro Glu Glu Arg Leu Arg Asn
        50                  55                  60

Leu Phe Ser Tyr Asp Gly Ile Trp Leu Phe Pro Lys Asn Gln Cys Lys
65                  70                  75                  80

Cys Glu Ala Asn Lys Glu Gln Gly Gly Tyr Asn Phe Gln Asp Ala Tyr
                85                  90                  95

Gly Gln Ser Asp Leu Pro Ala Val Lys Ala Arg Arg Gln Ala Glu Phe
            100                 105                 110

Glu His Phe Gln Arg Arg
        115
```

<210> SEQ ID NO 15
<211> LENGTH: 1361
<212> TYPE: DNA
<213> ORGANISM: Homo sapiens

<400> SEQUENCE: 15

```
atggggagcg ctggcttttc cgtgggaaaa ttccacgtgg aggtggcctc tcgcggccgg         60
gaatgtgtct cggggacgcc cgagtgtggg aatcggctcg ggagtgcggg cttcggggat        120
ctctgcttgg aactcagagg cgctgaccca gcctggggcc cgtttgctgc ccacggggag        180
agccgccgtc agggctcgag atttctgtgg ctcctcaaga tattggtcat aatcctggta        240
cttggcattg ttggattat gttcggaagc atgttcctcc aagcagtgtt cagcagcccc        300
aagccagaac tcccaagtcc tgccccgggt gtccagaagc tgaagcttct gcctgaggaa        360
cgtctcagga acctcttttc ctacgatgga atctgtcctc ttgcttgttt caggctgttc        420
ccgaaaaatc agtgcaaatg tgaagccaac aaagagcagg gaggttacaa ctttcaggat        480
gcctatggcc agagcgacct cccagcgtg aaagcgagga cagcggtga atttgaacac        540 tttcagagga gaagggct gccccgccca ctgcccctgc tggtccagcc caacctcccc        600
tttgggtacc cagtccacgg agtggaggtg atgcccctgc acacggttcc catcccaggc        660
ctccagtttg aaggacccga tgccccgtc tatgaggtca ccctgacagc ttctctgggg        720
acactgaaca cccttgctga tgtcccagac agtgtggtgc agggcagagg ccagaagcag        780
ctgatcattt ctaccagtga ccggaagctg ttgaagttca ttcttcagca cgtgacatac        840
accagcacgg ggtaccagca ccagaaggta gacatagtga gtctggagtc caggtccctca        900 gtggccaagt ttccagtgac catccgccat cctgtcatac ccaagctata cgaccctgga        960
ccagagagga agctcagaaa cctggttacc attgctacca agactttcct ccgcccccac       1020
```

```
aagctcatga tcatgctccg gagtattcga gagtattacc cagacttgac cgtaatagtg   1080
gctgatgaca gccagaagcc cctggaaatt aaagacaacc acgtggagta ttacactatg   1140 cccctttggga agggttggtt tgctggtagg aacctggcca tatctcaggt caccaccaaa   1200
tacgttctct gggtggacga tgattttctc ttcaacgagg agaccaagat tgaggtgctg   1260
gtggatgtcc tggagaaaac agaactggac gtggtaaggg acagttgcca gtttcaccca   1320
gccacaatct gtagagatgg agaagagggg agaagagagc g                      1361
```

<210> SEQ ID NO 16
<211> LENGTH: 453
<212> TYPE: PRT
<213> ORGANISM: Homo sapiens

<400> SEQUENCE: 16

```
Met Gly Ser Ala Gly Phe Ser Val Gly Lys Phe His Val Glu Val Ala
 1               5                  10                  15

Ser Arg Gly Arg Glu Cys Val Ser Gly Thr Pro Glu Cys Gly Asn Arg
            20                  25                  30

Leu Gly Ser Ala Gly Phe Gly Asp Leu Cys Leu Glu Leu Arg Gly Ala
        35                  40                  45

Asp Pro Ala Trp Gly Pro Phe Ala Ala His Gly Arg Ser Arg Arg Gln
    50                  55                  60

Gly Ser Arg Phe Leu Trp Leu Leu Lys Ile Leu Val Ile Ile Leu Val
65                  70                  75                  80

Leu Gly Ile Val Gly Phe Met Phe Gly Ser Met Phe Leu Gln Ala Val
                85                  90                  95

Phe Ser Ser Pro Lys Pro Glu Leu Pro Ser Pro Ala Pro Gly Val Gln
            100                 105                 110

Lys Leu Lys Leu Leu Pro Glu Glu Arg Leu Arg Asn Leu Phe Ser Tyr
        115                 120                 125

Asp Gly Ile Cys Pro Leu Ala Cys Phe Arg Leu Phe Pro Lys Asn Gln
    130                 135                 140

Cys Lys Cys Glu Ala Asn Lys Glu Gln Gly Gly Tyr Asn Phe Gln Asp
145                 150                 155                 160

Ala Tyr Gly Gln Ser Asp Leu Pro Ala Val Lys Ala Arg Arg Gln Ala
                165                 170                 175

Glu Phe Glu His Phe Gln Arg Arg Glu Gly Leu Pro Arg Pro Leu Pro
            180                 185                 190

Leu Leu Val Gln Pro Asn Leu Pro Phe Gly Tyr Pro Val His Gly Val
        195                 200                 205

Glu Val Met Pro Leu His Thr Val Pro Ile Pro Gly Leu Gln Phe Glu
    210                 215                 220

Gly Pro Asp Ala Pro Val Tyr Glu Val Thr Leu Thr Ala Ser Leu Gly
225                 230                 235                 240

Thr Leu Asn Thr Leu Ala Asp Val Pro Asp Ser Val Val Gln Gly Arg
                245                 250                 255

Gly Gln Lys Gln Leu Ile Ile Ser Thr Ser Asp Arg Lys Leu Leu Lys
            260                 265                 270

Phe Ile Leu Gln His Val Thr Tyr Thr Ser Thr Gly Tyr Gln His Gln
        275                 280                 285

Lys Val Asp Ile Val Ser Leu Glu Ser Arg Ser Ser Val Ala Lys Phe
    290                 295                 300

Pro Val Thr Ile Arg His Pro Val Ile Pro Lys Leu Tyr Asp Pro Gly
```

```
                305                 310                 315                 320
Pro Glu Arg Lys Leu Arg Asn Leu Val Thr Ile Ala Thr Lys Thr Phe
                325                 330                 335
Leu Arg Pro His Lys Leu Met Ile Met Leu Arg Ser Ile Arg Glu Tyr
                340                 345                 350
Tyr Pro Asp Leu Thr Val Ile Val Ala Asp Asp Ser Gln Lys Pro Leu
                355                 360                 365
Glu Ile Lys Asp Asn His Val Glu Tyr Tyr Thr Met Pro Phe Gly Lys
            370                 375                 380
Gly Trp Phe Ala Gly Arg Asn Leu Ala Ile Ser Gln Val Thr Thr Lys
385                 390                 395                 400
Tyr Val Leu Trp Val Asp Asp Phe Leu Phe Asn Glu Glu Thr Lys
                405                 410                 415
Ile Glu Val Leu Val Asp Val Leu Glu Lys Thr Glu Leu Asp Val Val
                420                 425                 430
Arg Asp Ser Cys Gln Phe His Pro Ala Thr Ile Cys Arg Asp Gly Glu
            435                 440                 445
Glu Gly Arg Arg Glu
        450

<210> SEQ ID NO 17
<211> LENGTH: 1181
<212> TYPE: DNA
<213> ORGANISM: Homo sapiens

<400> SEQUENCE: 17
atgacttcgg gcggctcgag atttctgtgg ctcctcaaga tattggtcat aatcctggta      60
cttggcattg ttggatttat gttcggaagc atgttccttc aagcagtgtt cagcagcccc     120
aagccagaac tcccaagtcc tgccccgggt gtccagaagc tgaagcttct gcctgaggaa     180
cgtctcagga acctcttttc ctacgatgga atctgtcctc ttgcttgttt caggctgttc     240
ccgaaaaatc agtgcaaatg tgaagccaac aaagagcagg gaggttacaa ctttcaggat     300
gcctatggcc agagcgacct cccagcggtg aaagcgagga caggctga atttgaacac      360
tttcagagga gagaagggct gccccgccca ctgcccctgc tggtccagcc caacctcccc     420
tttgggtacc cagtccacgg agtggagtg atgcccctgc acacggttcc catcccaggc      480
ctccagtttg aaggacccga tgcccccgtc tatgaggtca ccctgacagc ttctctgggg     540
acactgaaca cccttgctga tgtcccagac agtgtggtgc agggcagagg ccagaagcag     600
ctgatcattt ctaccagtga ccggaagctg ttgaagttca ttcttcagca cgtgacatac     660
accagcacgg ggtaccagca ccagaaggta gacatagtga gtctggagtc caggtcctca     720
gtggccaagt ttccagtgac catccgccat cctgtcatac ccaagctata cgaccctgga     780
ccagagagga agctcagaaa cctggttacc attgctacca gactttcct ccgcccccac      840
aagctcatga tcatgctccg gagtattcga gagtattacc cagacttgac cgtaatagtg     900
gctgatgaca gccagaagcc cctggaaatt aaagacaacc acgtggagta ttacactatg     960
ccctttggga agggttggtt tgctggtagg aacctggcca tatctcaggt caccaccaaa    1020
tacgttctct gggtggacga tgattttctc ttcaacgagg agaccaagat tgaggtgctg    1080
gtggatgtcc tggagaaaac agaactggac gtggtaaggg acagttgcca gtttcaccca    1140
gccacaatct gtagagatgg agaagagggg agaagagagc g                        1181

<210> SEQ ID NO 18
```

```
<211> LENGTH: 393
<212> TYPE: PRT
<213> ORGANISM: Homo sapiens

<400> SEQUENCE: 18

Met Thr Ser Gly Gly Ser Arg Phe Leu Trp Leu Leu Lys Ile Leu Val
 1               5                  10                  15

Ile Ile Leu Val Leu Gly Ile Val Gly Phe Met Phe Gly Ser Met Phe
                20                  25                  30

Leu Gln Ala Val Phe Ser Ser Pro Lys Pro Glu Leu Pro Ser Pro Ala
            35                  40                  45

Pro Gly Val Gln Lys Leu Lys Leu Leu Pro Glu Glu Arg Leu Arg Asn
        50                  55                  60

Leu Phe Ser Tyr Asp Gly Ile Cys Pro Leu Ala Cys Phe Arg Leu Phe
65                  70                  75                  80

Pro Lys Asn Gln Cys Lys Cys Glu Ala Asn Lys Glu Gln Gly Gly Tyr
                85                  90                  95

Asn Phe Gln Asp Ala Tyr Gly Gln Ser Asp Leu Pro Ala Val Lys Ala
            100                 105                 110

Arg Arg Gln Ala Glu Phe Glu His Phe Gln Arg Arg Glu Gly Leu Pro
        115                 120                 125

Arg Pro Leu Pro Leu Leu Val Gln Pro Asn Leu Pro Phe Gly Tyr Pro
130                 135                 140

Val His Gly Val Glu Val Met Pro Leu His Thr Val Pro Ile Pro Gly
145                 150                 155                 160

Leu Gln Phe Glu Gly Pro Asp Ala Pro Val Tyr Glu Val Thr Leu Thr
                165                 170                 175

Ala Ser Leu Gly Thr Leu Asn Thr Leu Ala Asp Val Pro Asp Ser Val
            180                 185                 190

Val Gln Gly Arg Gly Gln Lys Gln Leu Ile Ile Ser Thr Ser Asp Arg
        195                 200                 205

Lys Leu Leu Lys Phe Ile Leu Gln His Val Thr Tyr Thr Ser Thr Gly
210                 215                 220

Tyr Gln His Gln Lys Val Asp Ile Val Ser Leu Glu Ser Arg Ser Ser
225                 230                 235                 240

Val Ala Lys Phe Pro Val Thr Ile Arg His Pro Val Ile Pro Lys Leu
                245                 250                 255

Tyr Asp Pro Gly Pro Glu Arg Lys Leu Arg Asn Leu Val Thr Ile Ala
            260                 265                 270

Thr Lys Thr Phe Leu Arg Pro His Lys Leu Met Ile Met Leu Arg Ser
        275                 280                 285

Ile Arg Glu Tyr Tyr Pro Asp Leu Thr Val Ile Val Ala Asp Asp Ser
290                 295                 300

Gln Lys Pro Leu Glu Ile Lys Asp Asn His Val Glu Tyr Tyr Thr Met
305                 310                 315                 320

Pro Phe Gly Lys Gly Trp Phe Ala Gly Arg Asn Leu Ala Ile Ser Gln
                325                 330                 335

Val Thr Thr Lys Tyr Val Leu Trp Val Asp Asp Phe Leu Phe Asn
            340                 345                 350

Glu Glu Thr Lys Ile Glu Val Leu Val Asp Val Leu Lys Thr Glu
        355                 360                 365

Leu Asp Val Val Arg Asp Ser Cys Gln Phe His Pro Ala Thr Ile Cys
370                 375                 380

Arg Asp Gly Glu Glu Gly Arg Arg Glu
```

<210> SEQ ID NO 19
<211> LENGTH: 1344
<212> TYPE: DNA
<213> ORGANISM: Homo sapiens

<400> SEQUENCE: 19

```
atggggagcg ctggcttttc cgtgggaaaa ttccacgtgg aggtggcctc tcgcggccgg    60
gaatgtgtct cggggacgcc cgagtgtggg aatcggctcg ggagtgcggg cttcggggat   120
ctctgcttgg aactcagagg cgctgaccca gcctgggggcc cgtttgctgc ccacgggagg   180
agccgccgtc agggctcgag atttctgtgg ctcctcaaga tattggtcat aatcctggta   240
cttggcattg ttggatttat gttcggaagc atgttccttc aagcagtgtt cagcagcccc   300
aagccagaac tcccaagtcc tgccccgggt gtccagaagc tgaagcttct gcctgaggaa   360
cgtctcagga acctcttttc ctacgatgga atctggctgt cccgaaaaaa tcagtgcaaa   420
tgtgaagcca acaaagagca gggaggttac aactttcagg atgcctatgg ccagagcgac   480
ctcccagcgg tgaaagcgag agacaggct gaatttgaac actttcagag agagaaggg   540
ctgccccgcc cactgcccct gctggtccag cccaacctcc cctttgggta cccagtccac   600
ggagtggagg tgatgcccct gcacacggtt cccatcccag gcctccagtt tgaaggaccc   660
gatgccccg tctatgaggt caccctgaca gcttctctgg gacactgaa cacccttgct   720
gatgtcccag acagtgtggt gcagggcaga ggccagaagc agctgatcat ttctaccagt   780
gaccggaagc tgttgaagtt cattcttcag cacgtgacat acaccagcac ggggtaccag   840
caccagaagg tagacatagt gagtctggag tccaggtcct cagtggccaa gtttccagtg   900
accatccgcc atcctgtcat acccaagcta tacgaccctg accagagag gaagctcaga   960
aacctggtta ccattgctac caagactttc ctccgccccc acaagctcat gatcatgctc  1020
cggagtattc gagagtatta cccagacttg accgtaatag tggctgatga cagccagaag  1080
cccctggaaa ttaaagacaa ccacgtggag tattacacta tgcccctttgg gaaggggttgg  1140
tttgctggta ggaacctggc catatctcag gtcaccacca atacgttct ctgggtggac  1200
gatgattttc tcttcaacga ggagaccaag attgaggtgc tggtggatgt cctggagaaa  1260
acagaactgg acgtggtaag ggacagttgc cagtttcacc cagccacaat ctgtagagat  1320
ggagaagagg ggagaagaga gcga                                         1344
```

<210> SEQ ID NO 20
<211> LENGTH: 448
<212> TYPE: PRT
<213> ORGANISM: Homo sapiens

<400> SEQUENCE: 20

Met Gly Ser Ala Gly Phe Ser Val Gly Lys Phe His Val Glu Val Ala
1               5                   10                  15

Ser Arg Gly Arg Glu Cys Val Ser Gly Thr Pro Glu Cys Gly Asn Arg
            20                  25                  30

Leu Gly Ser Ala Gly Phe Gly Asp Leu Cys Leu Glu Leu Arg Gly Ala
        35                  40                  45

Asp Pro Ala Trp Gly Pro Phe Ala Ala His Gly Arg Ser Arg Arg Gln
    50                  55                  60

Gly Ser Arg Phe Leu Trp Leu Leu Lys Ile Leu Val Ile Ile Leu Val
65                  70                  75                  80

```
Leu Gly Ile Val Gly Phe Met Phe Gly Ser Met Phe Leu Gln Ala Val
                 85                  90                  95

Phe Ser Ser Pro Lys Pro Glu Leu Pro Ser Pro Ala Pro Gly Val Gln
                100                 105                 110

Lys Leu Lys Leu Leu Pro Glu Arg Leu Arg Asn Leu Phe Ser Tyr
                115                 120                 125

Asp Gly Ile Trp Leu Phe Pro Lys Asn Gln Cys Lys Cys Glu Ala Asn
130                 135                 140

Lys Glu Gln Gly Gly Tyr Asn Phe Gln Asp Ala Tyr Gly Gln Ser Asp
145                 150                 155                 160

Leu Pro Ala Val Lys Ala Arg Arg Gln Ala Glu Phe Glu His Phe Gln
                165                 170                 175

Arg Arg Glu Gly Leu Pro Arg Pro Leu Pro Leu Val Gln Pro Asn
                180                 185                 190

Leu Pro Phe Gly Tyr Pro Val His Gly Val Glu Val Met Pro Leu His
                195                 200                 205

Thr Val Pro Ile Pro Gly Leu Gln Phe Glu Gly Pro Asp Ala Pro Val
                210                 215                 220

Tyr Glu Val Thr Leu Thr Ala Ser Leu Gly Thr Leu Asn Thr Leu Ala
225                 230                 235                 240

Asp Val Pro Asp Ser Val Val Gln Gly Arg Gly Gln Lys Gln Leu Ile
                245                 250                 255

Ile Ser Thr Ser Asp Arg Lys Leu Leu Lys Phe Ile Leu Gln His Val
                260                 265                 270

Thr Tyr Thr Ser Thr Gly Tyr Gln His Gln Lys Val Asp Ile Val Ser
                275                 280                 285

Leu Glu Ser Arg Ser Ser Val Ala Lys Phe Pro Val Thr Ile Arg His
                290                 295                 300

Pro Val Ile Pro Lys Leu Tyr Asp Pro Gly Pro Glu Arg Lys Leu Arg
305                 310                 315                 320

Asn Leu Val Thr Ile Ala Thr Lys Thr Phe Leu Arg Pro His Lys Leu
                325                 330                 335

Met Ile Met Leu Arg Ser Ile Arg Glu Tyr Tyr Pro Asp Leu Thr Val
                340                 345                 350

Ile Val Ala Asp Asp Ser Gln Lys Pro Leu Glu Ile Lys Asp Asn His
                355                 360                 365

Val Glu Tyr Tyr Thr Met Pro Phe Gly Lys Gly Trp Phe Ala Gly Arg
                370                 375                 380

Asn Leu Ala Ile Ser Gln Val Thr Thr Lys Tyr Val Leu Trp Val Asp
385                 390                 395                 400

Asp Asp Phe Leu Phe Asn Glu Glu Thr Lys Ile Glu Val Leu Val Asp
                405                 410                 415

Val Leu Glu Lys Thr Glu Leu Asp Val Val Arg Asp Ser Cys Gln Phe
                420                 425                 430

His Pro Ala Thr Ile Cys Arg Asp Gly Glu Glu Gly Arg Arg Glu Arg
                435                 440                 445

<210> SEQ ID NO 21
<211> LENGTH: 1164
<212> TYPE: DNA
<213> ORGANISM: Homo sapiens

<400> SEQUENCE: 21
atgacttcgg gcggctcgag atttctgtgg ctcctcaaga tattggtcat aatcctggta      60
```

-continued

```
cttggcattg ttggatttat gttcggaagc atgttccttc aagcagtgtt cagcagcccc    120
aagccagaac tcccaagtcc tgccccgggt gtccagaagc tgaagcttct gcctgaggaa    180
cgtctcagga acctctttc ctacgatgga atctggctgt tcccgaaaaa tcagtgcaaa    240
tgtgaagcca acaaagagca gggaggttac aactttcagg atgcctatgg ccagagcgac    300
ctcccagcgg tgaaagcgag gagacaggct gaatttgaac actttcagag agagaagggg    360
ctgccccgcc cactgcccct gctggtccag cccaacctcc cctttgggta cccagtccac    420
ggagtggagg tgatgcccct gcacacggtt cccatcccag cctccagtt tgaaggaccc     480 gatgccccccg tctatgaggt caccctgaca gcttctctgg gacactgaa caccccttgct   540 gatgtcccag acagtgtggt gcagggcaga ggccagaagc agctgatcat ttctaccagt    600
gaccggaagc tgttgaagtt cattcttcag cacgtgacat acaccagcac ggggtaccag    660
caccagaagg tagacatagt gagtctggag tccaggtcct cagtggccaa gtttccagtg    720
accatccgcc atcctgtcat acccaagcta tacgaccctg gaccagagag gaagctcaga    780
aacctggtta ccattgctac caagactttc ctccgccccc acaagctcat gatcatgctc    840
cggagtattc gagagtatta cccagacttg accgtaatag tggctgatga cagccagaag    900
cccctggaaa ttaaagacaa ccacgtggag tattacacta tgccctttgg aaggggttgg    960
tttgctggta ggaacctggc catatctcag gtcaccacca aatacgttct ctgggtggac   1020 gatgatttc tcttcaacga ggagaccaag attgaggtgc tggtggatgt cctggagaaa   1080
acagaactgg acgtggtaag ggacagttgc cagtttcacc cagccacaat ctgtagagat   1140
ggagaagagg ggagaagaga gcga                                          1164
```

<210> SEQ ID NO 22
<211> LENGTH: 388
<212> TYPE: PRT
<213> ORGANISM: Homo sapiens

<400> SEQUENCE: 22

```
Met Thr Ser Gly Gly Ser Arg Phe Leu Trp Leu Leu Lys Ile Leu Val
  1               5                  10                  15

Ile Ile Leu Val Leu Gly Ile Val Gly Phe Met Phe Gly Ser Met Phe
             20                  25                  30

Leu Gln Ala Val Phe Ser Ser Pro Lys Pro Glu Leu Pro Ser Pro Ala
         35                  40                  45

Pro Gly Val Gln Lys Leu Lys Leu Leu Pro Glu Glu Arg Leu Arg Asn
     50                  55                  60

Leu Phe Ser Tyr Asp Gly Ile Trp Leu Phe Pro Lys Asn Gln Cys Lys
 65                  70                  75                  80

Cys Glu Ala Asn Lys Glu Gln Gly Gly Tyr Asn Phe Gln Asp Ala Tyr
                 85                  90                  95

Gly Gln Ser Asp Leu Pro Ala Val Lys Ala Arg Arg Gln Ala Glu Phe
            100                 105                 110

Glu His Phe Gln Arg Arg Glu Gly Leu Pro Arg Pro Leu Pro Leu Leu
        115                 120                 125

Val Gln Pro Asn Leu Pro Phe Gly Tyr Pro Val His Gly Val Glu Val
    130                 135                 140

Met Pro Leu His Thr Val Pro Ile Pro Gly Leu Gln Phe Glu Gly Pro
145                 150                 155                 160

Asp Ala Pro Val Tyr Glu Val Thr Leu Thr Ala Ser Leu Gly Thr Leu
                165                 170                 175
```

```
Asn Thr Leu Ala Asp Val Pro Asp Ser Val Gln Gly Arg Gly Gln
            180                 185                 190

Lys Gln Leu Ile Ile Ser Thr Ser Asp Arg Lys Leu Leu Lys Phe Ile
        195                 200                 205

Leu Gln His Val Thr Tyr Thr Ser Thr Gly Tyr Gln His Gln Lys Val
    210                 215                 220

Asp Ile Val Ser Leu Glu Ser Arg Ser Ser Val Ala Lys Phe Pro Val
225                 230                 235                 240

Thr Ile Arg His Pro Val Ile Pro Lys Leu Tyr Asp Pro Gly Pro Glu
                245                 250                 255

Arg Lys Leu Arg Asn Leu Val Thr Ile Ala Thr Lys Thr Phe Leu Arg
                260                 265                 270

Pro His Lys Leu Met Ile Met Leu Arg Ser Ile Arg Glu Tyr Tyr Pro
            275                 280                 285

Asp Leu Thr Val Ile Val Ala Asp Asp Ser Gln Lys Pro Leu Glu Ile
        290                 295                 300

Lys Asp Asn His Val Glu Tyr Tyr Thr Met Pro Phe Gly Lys Gly Trp
305                 310                 315                 320

Phe Ala Gly Arg Asn Leu Ala Ile Ser Gln Val Thr Thr Lys Tyr Val
                325                 330                 335

Leu Trp Val Asp Asp Asp Phe Leu Phe Asn Glu Thr Lys Ile Glu
                340                 345                 350

Val Leu Val Asp Val Leu Glu Lys Thr Glu Leu Asp Val Val Arg Asp
            355                 360                 365

Ser Cys Gln Phe His Pro Ala Thr Ile Cys Arg Asp Gly Glu Glu Gly
        370                 375                 380

Arg Arg Glu Arg
385

<210> SEQ ID NO 23
<211> LENGTH: 549
<212> TYPE: DNA
<213> ORGANISM: Homo sapiens

<400> SEQUENCE: 23
atggggagcg ctggcttttc cgtgggaaaa ttccacgtgg aggtggcctc tcgcggccgg     60
gaatgtgtct cggggacgcc cgagtgtggg aatcggctcg ggagtgcggg cttcggggat    120
ctctgcttgg aactcagagg cgctgaccca gcctggggcc cgtttgctgc ccacggggag    180
agccgccgtc agggctcgag atttctgtgg ctcctcaaga tattggtcat aatcctggta    240
cttggcattg ttgatttat gttcggaagc atgttccttc aagcagtgtt cagcagcccc    300
aagccagaac tcccaagtcc tgccccgggt gtccagaagc tgaagcttct gcctgaggaa    360
cgtctcagga acctcttttc ctacgatgga atctgtcctc ttgcttgttt caggctgttc    420
ccgaaaaatc agtgcaaatg tgaagccaac aaagagcagg gaggttacaa ctttcaggat    480
gcctatggcc agagcgacct cccagcggtg aaagcgagga gacaggctga atttgaacac    540
ccttgctga                                                            549

<210> SEQ ID NO 24
<211> LENGTH: 182
<212> TYPE: PRT
<213> ORGANISM: Homo sapiens

<400> SEQUENCE: 24

Met Gly Ser Ala Gly Phe Ser Val Gly Lys Phe His Val Glu Val Ala
```

-continued

```
              1               5                  10                 15
            Ser Arg Gly Arg Glu Cys Val Ser Gly Thr Pro Glu Cys Gly Asn Arg
                            20                 25                 30

Leu Gly Ser Ala Gly Phe Gly Asp Leu Cys Leu Glu Leu Arg Gly Ala
                        35                 40                 45

Asp Pro Ala Trp Gly Pro Phe Ala Ala His Gly Arg Ser Arg Arg Gln
                    50                 55                 60

Gly Ser Arg Phe Leu Trp Leu Lys Ile Leu Val Ile Ile Leu Val
            65                 70                 75                 80

Leu Gly Ile Val Gly Phe Met Phe Gly Ser Met Phe Leu Gln Ala Val
                                85                 90                 95

Phe Ser Ser Pro Lys Pro Glu Leu Pro Ser Pro Ala Pro Gly Val Gln
                            100                105                110

Lys Leu Lys Leu Leu Pro Glu Glu Arg Leu Arg Asn Leu Phe Ser Tyr
                        115                120                125

Asp Gly Ile Cys Pro Leu Ala Cys Phe Arg Leu Phe Pro Lys Asn Gln
                    130                135                140

Cys Lys Cys Glu Ala Asn Lys Glu Gln Gly Gly Tyr Asn Phe Gln Asp
            145                150                155                160

Ala Tyr Gly Gln Ser Asp Leu Pro Ala Val Lys Ala Arg Arg Gln Ala
                                165                170                175

Glu Phe Glu His Pro Cys
                        180

<210> SEQ ID NO 25
<211> LENGTH: 369
<212> TYPE: DNA
<213> ORGANISM: Homo sapiens

<400> SEQUENCE: 25
atgacttcgg gcggctcgag atttctgtgg ctcctcaaga tattggtcat aatcctggta        60
cttggcattg ttggatttat gttcggaagc atgttcctt c aagcagtgtt cagcagcccc      120
aagccagaac tcccaagtcc tgccccgggt gtccagaagc tgaagcttct gcctgaggaa      180
cgtctcagga acctcttttc ctacgatgga atctgtcctc ttgcttgttt caggctgttc      240
ccgaaaaatc agtgcaaatg tgaagccaac aaagagcagg gaggttacaa ctttcaggat      300
gcctatggcc agagcgacct cccagcggtg aaagcgagga caggctga atttgaacac      360 ccttgctga                                                                369

<210> SEQ ID NO 26
<211> LENGTH: 122
<212> TYPE: PRT
<213> ORGANISM: Homo sapiens

<400> SEQUENCE: 26

Met Thr Ser Gly Gly Ser Arg Phe Leu Trp Leu Leu Lys Ile Leu Val
1               5                  10                 15

Ile Ile Leu Val Leu Gly Ile Val Gly Phe Met Phe Gly Ser Met Phe
                20                 25                 30

Leu Gln Ala Val Phe Ser Ser Pro Lys Pro Glu Leu Pro Ser Pro Ala
            35                 40                 45

Pro Gly Val Gln Lys Leu Lys Leu Leu Pro Glu Glu Arg Leu Arg Asn
        50                 55                 60

Leu Phe Ser Tyr Asp Gly Ile Cys Pro Leu Ala Cys Phe Arg Leu Phe
65                 70                 75                 80
```

```
Pro Lys Asn Gln Cys Lys Cys Glu Ala Asn Lys Glu Gln Gly Gly Tyr
            85                  90                  95

Asn Phe Gln Asp Ala Tyr Gly Gln Ser Asp Leu Pro Ala Val Lys Ala
            100                 105                 110

Arg Arg Gln Ala Glu Phe Glu His Pro Cys
            115                 120
```

<210> SEQ ID NO 27
<211> LENGTH: 531
<212> TYPE: DNA
<213> ORGANISM: Homo sapiens

<400> SEQUENCE: 27

```
atggggagcg ctggcttttc cgtgggaaaa ttccacgtgg aggtggcctc tcgcggccgg     60
gaatgtgtct cggggacgcc cgagtgtggg aatcggctcg ggagtgcggg cttcggggat    120
ctctgcttgg aactcagagg cgctgaccca gcctgggggcc cgtttgctgc ccacggggag    180
agccgccgtc agggctcgag atttctgtgg ctcctcaaga tattggtcat aatcctggta    240
cttggcattg ttgatttat gttcggaagc atgttccttc aagcagtgtt cagcagcccc    300
aagccagaac tcccaagtcc tgccccgggt gtccagaagc tgaagcttct gcctgaggaa    360
cgtctcagga acctcttttc ctacgatgga atctggctgt tcccgaaaaa tcagtgcaaa    420
tgtgaagcca acaaagagca gggaggttac aactttcagg atgcctatgg ccagagcgac    480
ctcccagcgg tgaaagcgag gagacaggct gaatttgaac cccttgctg a              531
```

<210> SEQ ID NO 28
<211> LENGTH: 176
<212> TYPE: PRT
<213> ORGANISM: Homo sapiens

<400> SEQUENCE: 28

```
Met Gly Ser Ala Gly Phe Ser Val Gly Lys Phe His Val Glu Val Ala
1               5                   10                  15

Ser Arg Gly Arg Glu Cys Val Ser Gly Thr Pro Glu Cys Gly Asn Arg
            20                  25                  30

Leu Gly Ser Ala Gly Phe Gly Asp Leu Cys Leu Glu Leu Arg Gly Ala
        35                  40                  45

Asp Pro Ala Trp Gly Pro Phe Ala Ala His Gly Arg Ser Arg Arg Gln
    50                  55                  60

Gly Ser Arg Phe Leu Trp Leu Leu Lys Ile Leu Val Ile Ile Leu Val
65                  70                  75                  80

Leu Gly Ile Val Gly Phe Met Phe Gly Ser Met Phe Leu Gln Ala Val
                85                  90                  95

Phe Ser Ser Pro Lys Pro Glu Leu Pro Ser Pro Ala Pro Gly Val Gln
            100                 105                 110

Lys Leu Lys Leu Leu Pro Glu Glu Arg Leu Arg Asn Leu Phe Ser Tyr
        115                 120                 125

Asp Gly Ile Trp Leu Phe Pro Lys Asn Gln Cys Lys Cys Glu Ala Asn
    130                 135                 140

Lys Glu Gln Gly Gly Tyr Asn Phe Gln Asp Ala Tyr Gly Gln Ser Asp
145                 150                 155                 160

Leu Pro Ala Val Lys Ala Arg Arg Gln Ala Glu Phe Glu His Pro Cys
                165                 170                 175
```

<210> SEQ ID NO 29

<211> LENGTH: 351
<212> TYPE: DNA
<213> ORGANISM: Homo sapiens

<400> SEQUENCE: 29

```
atgacttcgg gcggctcgag atttctgtgg ctcctcaaga tattggtcat aatcctggta      60
cttggcattg ttggatttat gttcggaagc atgttccttc aagcagtgtt cagcagcccc     120
aagccagaac tcccaagtcc tgccccgggt gtccagaagc tgaagcttct gcctgaggaa     180
cgtctcagga acctcttttc ctacgatgga atctggctgt tcccgaaaaa tcagtgcaaa     240
tgtgaagcca acaaagagca gggaggttac aactttcagg atgcctatgg ccagagcgac     300
ctcccagcgg tgaaagcgag gagacaggct gaatttgaac accttgctg a               351
```

<210> SEQ ID NO 30
<211> LENGTH: 116
<212> TYPE: PRT
<213> ORGANISM: Homo sapiens

<400> SEQUENCE: 30

```
Met Thr Ser Gly Gly Ser Arg Phe Leu Trp Leu Leu Lys Ile Leu Val
  1               5                  10                  15

Ile Ile Leu Val Leu Gly Ile Val Gly Phe Met Phe Gly Ser Met Phe
             20                  25                  30

Leu Gln Ala Val Phe Ser Ser Pro Lys Pro Glu Leu Pro Ser Pro Ala
         35                  40                  45

Pro Gly Val Gln Lys Leu Lys Leu Leu Pro Glu Glu Arg Leu Arg Asn
     50                  55                  60

Leu Phe Ser Tyr Asp Gly Ile Trp Leu Phe Pro Lys Asn Gln Cys Lys
 65                  70                  75                  80

Cys Glu Ala Asn Lys Glu Gln Gly Gly Tyr Asn Phe Gln Asp Ala Tyr
                 85                  90                  95

Gly Gln Ser Asp Leu Pro Ala Val Lys Ala Arg Arg Gln Ala Glu Phe
            100                 105                 110

Glu His Pro Cys
            115
```

<210> SEQ ID NO 31
<211> LENGTH: 1719
<212> TYPE: DNA
<213> ORGANISM: Homo sapiens

<400> SEQUENCE: 31

```
atggggagcg ctggcttttc cgtgggaaaa ttccacgtgg aggtggcctc tcgcggccgg      60
gaatgtgtct cggggacgcc cgagtgtggg aatcggctcg ggagtgcggg cttcggggat     120
ctctgcttgg aactcagagg cgctgaccca gcctggggcc cgtttgctgc cacgggagg      180
agccgccgtc agggctcgag atttctgtgg ctcctcaaga tattggtcat aatcctggta     240
cttggcattg ttggatttat gttcggaagc atgttccttc aagcagtgtt cagcagcccc     300
aagccagaac tcccaagtcc tgccccgggt gtccagaagc tgaagcttct gcctgaggaa     360
cgtctcagga acctcttttc ctacgatgga atctgtcctc ttgcttgttt caggctgttc     420
ccgaaaaatc agtgcaaatg tgaagccaac aaagagcagg gaggttacaa ctttcaggat     480
gcctatggcc agagcgacct cccagcggtg aaagcgagga gacaggctga atttgaacac     540
tttcagagga gagaagggct gccccgccca ctgcccctgc tggtccagcc caacctcccc     600
tttgggtacc cagtccacgg agtggaggtg atgccccctgc acacggttcc catcccaggc     660
```

-continued

```
ctccagtttg aaggacccga tgcccccgtc tatgaggtca ccctgacagc ttctctgggg      720
acactgaaca cccttgctga tgtcccagac agtgtggtgc agggcagagg ccagaagcag      780
ctgatcattt ctaccagtga ccggaagctg ttgaagttca ttcttcagca cgtgacatac      840
accagcacgg ggtaccagca ccagaaggta gacatagtga gtctggagtc caggtcctca      900
gtggccaagt ttccagtgac catccgccat cctgtcatac ccaagctata cgaccctgga      960
ccagagagga agctcagaaa cctggttacc attgctacca agactttcct ccgcccccac     1020
aagctcatga tcatgctccg gagtattcga gagtattacc agacttgac cgtaatagtg      1080 gctgatgaca gccagaagcc cctggaaatt aaagacaacc acgtggagta ttacactatg     1140
ccctttggga agggttggtt tgctggtagg aacctggcca tatctcaggt caccaccaaa     1200
tacgttctct gggtggacga tgattttctc ttcaacgagg agaccaagat tgaggtgctg     1260
gtggatgtcc tggagaaaac agaactggac gtggtaggcg gcagtgtgct gggaaatgtg     1320
ttccagttta agttgttgct ggaacagagt gagaatgggg cctgccttca agaggatg      1380 ggatttttcc aaccctggac tggcttcccc agctgcgtgg tgaccagtgg cgtggtcaac     1440
ttcttcctgg cccacacgga gcgactccaa agagttggct tgatccccg cctgcaacga      1500 gtggctcact cagaattctt cattgatggg ctagggaccc tactcgtggg gtcatgccca     1560
gaagtgatta taggtcacca gtctcggtct ccagtggtgg actcagaact ggctgccta     1620 gagaagacct acaatacata ccggtccaac accctcaccc gggtccagtt caagctggcc     1680
cttcactact tcaagaacca tctccaatgt gccgcataa                             1719
```

<210> SEQ ID NO 32
<211> LENGTH: 572
<212> TYPE: PRT
<213> ORGANISM: Homo sapiens

<400> SEQUENCE: 32

```
Met Gly Ser Ala Gly Phe Ser Val Gly Lys Phe His Val Glu Val Ala
 1               5                  10                  15

Ser Arg Gly Arg Glu Cys Val Ser Gly Thr Pro Glu Cys Gly Asn Arg
            20                  25                  30

Leu Gly Ser Ala Gly Phe Gly Asp Leu Cys Leu Glu Leu Arg Gly Ala
        35                  40                  45

Asp Pro Ala Trp Gly Pro Phe Ala Ala His Gly Arg Ser Arg Arg Gln
    50                  55                  60

Gly Ser Arg Phe Leu Trp Leu Leu Lys Ile Leu Val Ile Ile Leu Val
65                  70                  75                  80

Leu Gly Ile Val Gly Phe Met Phe Gly Ser Met Phe Leu Gln Ala Val
                85                  90                  95

Phe Ser Ser Pro Lys Pro Glu Leu Pro Ser Pro Ala Pro Gly Val Gln
            100                 105                 110

Lys Leu Lys Leu Leu Pro Glu Glu Arg Leu Arg Asn Leu Phe Ser Tyr
        115                 120                 125

Asp Gly Ile Cys Pro Leu Ala Cys Phe Arg Leu Phe Pro Lys Asn Gln
    130                 135                 140

Cys Lys Cys Glu Ala Asn Lys Glu Gln Gly Gly Tyr Asn Phe Gln Asp
145                 150                 155                 160

Ala Tyr Gly Gln Ser Asp Leu Pro Ala Val Lys Ala Arg Arg Gln Ala
                165                 170                 175

Glu Phe Glu His Phe Gln Arg Arg Glu Gly Leu Pro Arg Pro Leu Pro
```

```
                    180                 185                 190
Leu Leu Val Gln Pro Asn Leu Pro Phe Gly Tyr Pro Val His Gly Val
            195                 200                 205
Glu Val Met Pro Leu His Thr Val Pro Ile Pro Gly Leu Gln Phe Glu
        210                 215                 220
Gly Pro Asp Ala Pro Val Tyr Glu Val Thr Leu Thr Ala Ser Leu Gly
225                 230                 235                 240
Thr Leu Asn Thr Leu Ala Asp Val Pro Asp Ser Val Val Gln Gly Arg
                245                 250                 255
Gly Gln Lys Gln Leu Ile Ile Ser Thr Ser Asp Arg Lys Leu Leu Lys
            260                 265                 270
Phe Ile Leu Gln His Val Thr Tyr Thr Ser Thr Gly Tyr Gln His Gln
        275                 280                 285
Lys Val Asp Ile Val Ser Leu Glu Ser Arg Ser Ser Val Ala Lys Phe
    290                 295                 300
Pro Val Thr Ile Arg His Pro Val Ile Pro Lys Leu Tyr Asp Pro Gly
305                 310                 315                 320
Pro Glu Arg Lys Leu Arg Asn Leu Val Thr Ile Ala Thr Lys Thr Phe
                325                 330                 335
Leu Arg Pro His Lys Leu Met Ile Met Leu Arg Ser Ile Arg Glu Tyr
            340                 345                 350
Tyr Pro Asp Leu Thr Val Ile Val Ala Asp Asp Ser Gln Lys Pro Leu
        355                 360                 365
Glu Ile Lys Asp Asn His Val Glu Tyr Tyr Thr Met Pro Phe Gly Lys
    370                 375                 380
Gly Trp Phe Ala Gly Arg Asn Leu Ala Ile Ser Gln Val Thr Thr Lys
385                 390                 395                 400
Tyr Val Leu Trp Val Asp Asp Asp Phe Leu Phe Asn Glu Glu Thr Lys
                405                 410                 415
Ile Glu Val Leu Val Asp Val Leu Glu Lys Thr Glu Leu Asp Val Val
            420                 425                 430
Gly Gly Ser Val Leu Gly Asn Val Phe Gln Phe Lys Leu Leu Leu Glu
        435                 440                 445
Gln Ser Glu Asn Gly Ala Cys Leu His Lys Arg Met Gly Phe Phe Gln
    450                 455                 460
Pro Leu Asp Gly Phe Pro Ser Cys Val Val Thr Ser Gly Val Val Asn
465                 470                 475                 480
Phe Phe Leu Ala His Thr Glu Arg Leu Gln Arg Val Gly Phe Asp Pro
                485                 490                 495
Arg Leu Gln Arg Val Ala His Ser Glu Phe Phe Ile Asp Gly Leu Gly
            500                 505                 510
Thr Leu Leu Val Gly Ser Cys Pro Glu Val Ile Ile Gly His Gln Ser
        515                 520                 525
Arg Ser Pro Val Val Asp Ser Glu Leu Ala Ala Leu Glu Lys Thr Tyr
    530                 535                 540
Asn Thr Tyr Arg Ser Asn Thr Leu Thr Arg Val Gln Phe Lys Leu Ala
545                 550                 555                 560
Leu His Tyr Phe Lys Asn His Leu Gln Cys Ala Ala
                565                 570

<210> SEQ ID NO 33
<211> LENGTH: 1539
<212> TYPE: DNA
<213> ORGANISM: Homo sapiens
```

-continued

<400> SEQUENCE: 33

```
atgacttcgg gcggctcgag atttctgtgg ctcctcaaga tattggtcat aatcctggta      60
cttggcattg ttggatttat gttcggaagc atgttccttc aagcagtgtt cagcagcccc     120
aagccagaac tcccaagtcc tgccccgggt gtccagaagc tgaagcttct gcctgaggaa     180
cgtctcagga acctcttttc ctacgatgga atctgtcctc ttgcttgttt caggctgttc     240
ccgaaaaatc agtgcaaatg tgaagccaac aaagagcagg gaggttacaa ctttcaggat     300
gcctatggcc agagcgacct cccagcggtg aaagcgagga caggctgaa atttgaacac      360
tttcagagga gagaagggct gccccgccca ctgcccctgc tggtccagcc aacctcccc      420
tttgggtacc cagtccacgg agtggaggtg atgcccctgc acacggttcc catcccaggc     480
ctccagtttg aaggacccga tgccccgtc tatgaggtca ccctgacagc ttctctgggg      540
acactgaaca cccttgctga tgtcccagac agtgtggtgc agggcagagg ccagaagcag     600
ctgatcattt ctaccagtga ccggaagctg ttgaagttca ttcttcagca cgtgacatac     660
accagcacgg gtaccagca ccagaaggta gacatagtga gtctggagtc caggtcctca     720
gtggccaagt ttccagtgac catccgccat cctgtcatac ccaagctata cgaccctgga     780
ccagagagga agctcagaaa cctggttacc attgctacca agactttcct ccgcccccac     840
aagctcatga tcatgctccg gagtattcga gagtattacc cagacttgac cgtaatagtg     900
gctgatgaca gccagaagcc cctggaaatt aagacaacc acgtggagta ttacactatg      960
ccctttggga agggttggtt tgctggtagg aacctggcca tatctcaggt caccaccaaa    1020
tacgttctct gggtggacga tgattttctc ttcaacgagg agaccaagat tgaggtgctg    1080
gtggatgtcc tggagaaaac agaactggac gtggtaggcg gcagtgtgct gggaaatgtg    1140
ttccagttta gttgttgct ggaacagagt gagaatgggg cctgccttca aagaggatg     1200
ggatttttcc aaccctgga tggcttcccc agctgcgtgg tgaccagtgg cgtggtcaac    1260
ttcttcctgg cccacacgga gcgactccaa agagttggct tgatcccg cctgcaacga      1320
gtggctcact cagaattctt cattgatggg ctagggaccc tactcgtggg gtcatgccca    1380
gaagtgatta taggtcacca gtctcggtct ccagtggtgg actcagaact ggctgcccta    1440
gagaagacct acaatacata ccggtccaac accctcaccc gggtccagtt caagctggcc    1500
cttcactact tcaagaacca tctccaatgt gccgcataa                            1539
```

<210> SEQ ID NO 34
<211> LENGTH: 512
<212> TYPE: PRT
<213> ORGANISM: Homo sapiens

<400> SEQUENCE: 34

```
Met Thr Ser Gly Gly Ser Arg Phe Leu Trp Leu Leu Lys Ile Leu Val
  1               5                  10                  15

Ile Ile Leu Val Leu Gly Ile Val Gly Phe Met Phe Gly Ser Met Phe
             20                  25                  30

Leu Gln Ala Val Phe Ser Ser Pro Lys Pro Glu Leu Pro Ser Pro Ala
         35                  40                  45

Pro Gly Val Gln Lys Leu Lys Leu Leu Pro Glu Glu Arg Leu Arg Asn
     50                  55                  60

Leu Phe Ser Tyr Asp Gly Ile Cys Pro Leu Ala Cys Phe Arg Leu Phe
 65                  70                  75                  80

Pro Lys Asn Gln Cys Lys Cys Glu Ala Asn Lys Glu Gln Gly Gly Tyr
```

-continued

```
                    85                  90                  95
Asn Phe Gln Asp Ala Tyr Gly Gln Ser Asp Leu Pro Ala Val Lys Ala
                100                 105                 110
Arg Arg Gln Ala Glu Phe Glu His Phe Gln Arg Arg Glu Gly Leu Pro
            115                 120                 125
Arg Pro Leu Pro Leu Val Gln Pro Asn Leu Pro Phe Gly Tyr Pro
        130                 135                 140
Val His Gly Val Glu Val Met Pro Leu His Thr Val Pro Ile Pro Gly
145                 150                 155                 160
Leu Gln Phe Glu Gly Pro Asp Ala Pro Val Tyr Glu Val Thr Leu Thr
                165                 170                 175
Ala Ser Leu Gly Thr Leu Asn Thr Leu Ala Asp Val Pro Asp Ser Val
            180                 185                 190
Val Gln Gly Arg Gly Gln Lys Gln Leu Ile Ile Ser Thr Ser Asp Arg
        195                 200                 205
Lys Leu Leu Lys Phe Ile Leu Gln His Val Thr Tyr Thr Ser Thr Gly
210                 215                 220
Tyr Gln His Gln Lys Val Asp Ile Val Ser Leu Glu Ser Arg Ser Ser
225                 230                 235                 240
Val Ala Lys Phe Pro Val Thr Ile Arg His Pro Val Ile Pro Lys Leu
                245                 250                 255
Tyr Asp Pro Gly Pro Glu Arg Lys Leu Arg Asn Leu Val Thr Ile Ala
            260                 265                 270
Thr Lys Thr Phe Leu Arg Pro His Lys Leu Met Ile Met Leu Arg Ser
        275                 280                 285
Ile Arg Glu Tyr Tyr Pro Asp Leu Thr Val Ile Val Ala Asp Asp Ser
        290                 295                 300
Gln Lys Pro Leu Glu Ile Lys Asp Asn His Val Glu Tyr Tyr Thr Met
305                 310                 315                 320
Pro Phe Gly Lys Gly Trp Phe Ala Gly Arg Asn Leu Ala Ile Ser Gln
                325                 330                 335
Val Thr Thr Lys Tyr Val Leu Trp Val Asp Asp Asp Phe Leu Phe Asn
            340                 345                 350
Glu Glu Thr Lys Ile Glu Val Leu Val Asp Val Leu Glu Lys Thr Glu
        355                 360                 365
Leu Asp Val Val Gly Gly Ser Val Leu Gly Asn Val Phe Gln Phe Lys
    370                 375                 380
Leu Leu Leu Glu Gln Ser Glu Asn Gly Ala Cys Leu His Lys Arg Met
385                 390                 395                 400
Gly Phe Phe Gln Pro Leu Asp Gly Phe Pro Ser Cys Val Val Thr Ser
                405                 410                 415
Gly Val Val Asn Phe Phe Leu Ala His Thr Glu Arg Leu Gln Arg Val
            420                 425                 430
Gly Phe Asp Pro Arg Leu Gln Arg Val Ala His Ser Glu Phe Phe Ile
        435                 440                 445
Asp Gly Leu Gly Thr Leu Leu Val Gly Ser Cys Pro Glu Val Ile Ile
    450                 455                 460
Gly His Gln Ser Arg Ser Pro Val Val Asp Ser Glu Leu Ala Ala Leu
465                 470                 475                 480
Glu Lys Thr Tyr Asn Thr Tyr Arg Ser Asn Thr Leu Thr Arg Val Gln
                485                 490                 495
Phe Lys Leu Ala Leu His Tyr Phe Lys Asn His Leu Gln Cys Ala Ala
            500                 505                 510
```

<210> SEQ ID NO 35
<211> LENGTH: 1701
<212> TYPE: DNA
<213> ORGANISM: Homo sapiens

<400> SEQUENCE: 35

| | |
|---|---|
| atggggagcg ctggcttttc cgtgggaaaa ttccacgtgg aggtggcctc tcgcggccgg | 60 |
| gaatgtgtct cggggacgcc cgagtgtggg aatcggctcg ggagtgcggg cttcggggat | 120 |
| ctctgcttgg aactcagagg cgctgaccca gcctggggcc cgtttgctgc ccacggggag | 180 |
| agccgccgtc agggctcgag atttctgtgg ctcctcaaga tattggtcat aatcctggta | 240 |
| cttggcattg ttggatttat gttcggaagc atgttccttc aagcagtgtt cagcagcccc | 300 |
| aagccagaac tcccaagtcc tgccccgggt gtccagaagc tgaagcttct gcctgaggaa | 360 |
| cgtctcagga acctcttttc ctacgatgga atctggctgt tccgaaaaa tcagtgcaaa | 420 |
| tgtgaagcca caaagagca gggaggttac aactttcagg atgcctatgg ccagagcgac | 480 |
| ctcccagcgt gaaagcgag gagacaggct gaatttgaac actttcagag agagaaggg | 540 |
| ctgccccgcc cactgcccct gctggtccag cccaacctcc cctttgggta cccagtccac | 600 |
| ggagtggagg tgatgcccct gcacacggtt cccatcccag gcctccagtt tgaaggaccc | 660 |
| gatgcccccg tctatgaggt caccctgaca gcttctctgg gacactgaa caccctttgct | 720 |
| gatgtccccag acagtgtggt gcagggcaga ggccagaagc agctgatcat ttctaccagt | 780 |
| gaccggaagc tgttgaagtt cattcttcag cacgtgacat acaccagcac ggggtaccag | 840 |
| caccagaagg tagacatagt gagtctggag tccaggtcct cagtggccaa gtttccagtg | 900 |
| accatccgcc atcctgtcat acccaagcta tacgaccctg gaccagagag gaagctcaga | 960 |
| aacctggtta ccattgctac caagactttc ctccgccccc acaagctcat gatcatgctc | 1020 |
| cggagtattc gagagtatta cccagacttg accgtaatag tggctgatga cagccagaag | 1080 |
| cccctggaaa ttaaagacaa ccacgtggag tattacacta tgcccttttgg gaagggttgg | 1140 |
| tttgctggta ggaacctggc catatctcag gtcaccacca aatacgttct ctgggtggac | 1200 |
| gatgatttc tcttcaacga ggagaccaag attgaggtgc tggtggatgt cctggagaaa | 1260 |
| acagaactgg acgtggtagg cggcagtgtg ctgggaaatg tgttccagtt taagttgttg | 1320 |
| ctggaacaga gtgagaatgg ggcctgcctt cacaagagga tgggatttt ccaacccctg | 1380 |
| gatggcttcc ccagctgcgt ggtgaccagt ggcgtggtca acttcttcct ggcccacacg | 1440 |
| gagcgactcc aaagagttgg ctttgatccc cgcctgcaac gagtggctca ctcagaattc | 1500 |
| ttcattgatg ggctagggac cctactcgtg gggtcatgcc cagaagtgat tataggtcac | 1560 |
| cagtctcggt ctccagtggt ggactcagaa ctggctgccc tagagaagac ctacaataca | 1620 |
| taccggtcca acaccctcac ccgggtccag ttcaagctgg cccttcacta cttcaagaac | 1680 |
| catctccaat gtgccgcata a | 1701 |

<210> SEQ ID NO 36
<211> LENGTH: 566
<212> TYPE: PRT
<213> ORGANISM: Homo sapiens

<400> SEQUENCE: 36

Met Gly Ser Ala Gly Phe Ser Val Gly Lys Phe His Val Glu Val Ala
 1               5                  10                  15

Ser Arg Gly Arg Glu Cys Val Ser Gly Thr Pro Glu Cys Gly Asn Arg

-continued

```
             20                  25                  30
Leu Gly Ser Ala Gly Phe Gly Asp Leu Cys Leu Glu Leu Arg Gly Ala
             35                  40                  45

Asp Pro Ala Trp Gly Pro Phe Ala Ala His Gly Arg Ser Arg Arg Gln
 50                  55                  60

Gly Ser Arg Phe Leu Trp Leu Leu Lys Ile Leu Val Ile Ile Leu Val
 65                  70                  75                  80

Leu Gly Ile Val Gly Phe Met Phe Gly Ser Met Phe Leu Gln Ala Val
                 85                  90                  95

Phe Ser Ser Pro Lys Pro Glu Leu Pro Ser Pro Ala Pro Gly Val Gln
                100                 105                 110

Lys Leu Lys Leu Leu Pro Glu Glu Arg Leu Arg Asn Leu Phe Ser Tyr
                115                 120                 125

Asp Gly Ile Trp Leu Phe Pro Lys Asn Gln Cys Lys Cys Glu Ala Asn
                130                 135                 140

Lys Glu Gln Gly Gly Tyr Asn Phe Gln Asp Ala Tyr Gly Gln Ser Asp
145                 150                 155                 160

Leu Pro Ala Val Lys Ala Arg Arg Gln Ala Glu Phe Glu His Phe Gln
                165                 170                 175

Arg Arg Glu Gly Leu Pro Arg Pro Leu Pro Leu Val Gln Pro Asn
                180                 185                 190

Leu Pro Phe Gly Tyr Pro Val His Gly Val Glu Val Met Pro Leu His
                195                 200                 205

Thr Val Pro Ile Pro Gly Leu Gln Phe Glu Gly Pro Asp Ala Pro Val
                210                 215                 220

Tyr Glu Val Thr Leu Thr Ala Ser Leu Gly Thr Leu Asn Thr Leu Ala
225                 230                 235                 240

Asp Val Pro Asp Ser Val Val Gln Gly Arg Gly Gln Lys Gln Leu Ile
                245                 250                 255

Ile Ser Thr Ser Asp Arg Lys Leu Leu Lys Phe Ile Leu Gln His Val
                260                 265                 270

Thr Tyr Thr Ser Thr Gly Tyr Gln His Gln Lys Val Asp Ile Val Ser
                275                 280                 285

Leu Glu Ser Arg Ser Ser Val Ala Lys Phe Pro Val Thr Ile Arg His
                290                 295                 300

Pro Val Ile Pro Lys Leu Tyr Asp Pro Gly Pro Glu Arg Lys Leu Arg
305                 310                 315                 320

Asn Leu Val Thr Ile Ala Thr Lys Thr Phe Leu Arg Pro His Lys Leu
                325                 330                 335

Met Ile Met Leu Arg Ser Ile Arg Glu Tyr Tyr Pro Asp Leu Thr Val
                340                 345                 350

Ile Val Ala Asp Asp Ser Gln Lys Pro Leu Glu Ile Lys Asp Asn His
                355                 360                 365

Val Glu Tyr Tyr Thr Met Pro Phe Gly Lys Gly Trp Phe Ala Gly Arg
                370                 375                 380

Asn Leu Ala Ile Ser Gln Val Thr Thr Lys Tyr Val Leu Trp Val Asp
385                 390                 395                 400

Asp Asp Phe Leu Phe Asn Glu Glu Thr Lys Ile Glu Val Leu Val Asp
                405                 410                 415

Val Leu Glu Lys Thr Glu Leu Asp Val Val Gly Gly Ser Val Leu Gly
                420                 425                 430

Asn Val Phe Gln Phe Lys Leu Leu Leu Glu Gln Ser Glu Asn Gly Ala
                435                 440                 445
```

-continued

```
Cys Leu His Lys Arg Met Gly Phe Phe Gln Pro Leu Asp Gly Phe Pro
    450                 455                 460
Ser Cys Val Val Thr Ser Gly Val Val Asn Phe Leu Ala His Thr
465                 470                 475                 480
Glu Arg Leu Gln Arg Val Gly Phe Asp Pro Arg Leu Gln Arg Val Ala
                485                 490                 495
His Ser Glu Phe Phe Ile Asp Gly Leu Gly Thr Leu Leu Val Gly Ser
            500                 505                 510
Cys Pro Glu Val Ile Ile Gly His Gln Ser Arg Ser Pro Val Val Asp
        515                 520                 525
Ser Glu Leu Ala Ala Leu Glu Lys Thr Tyr Asn Thr Tyr Arg Ser Asn
530                 535                 540
Thr Leu Thr Arg Val Gln Phe Lys Leu Ala Leu His Tyr Phe Lys Asn
545                 550                 555                 560
His Leu Gln Cys Ala Ala
            565
```

<210> SEQ ID NO 37
<211> LENGTH: 3244
<212> TYPE: DNA
<213> ORGANISM: Homo sapiens

<400> SEQUENCE: 37

```
ggcggcctgg ctgctaggct ccgtgacatc cggcagtctg agggcggcgg gattcgggat      60
gacttcgggc gggtgagtgt cctcggggca gagcaaaagc gagaggtgaa acttcgggag     120
cagggagcgc cgcgggtcct ttctggcgtc tgcagagcgg gcaggtgctg gggacgcaga     180
cgccggagcc agggagcggg cggttggagt cttaagtcca accggttccc cgcataggtg     240
gctgcagagg cgaggtgacg gcgcgtgcgg aacgaactct gcaccccag gaatggggag      300
cgctggcttt tccgtgggaa aattccacgt ggaggtggcc tctcgcggcc gggaatgtgt     360
ctcggggacg cccgagtgtg ggaatcggct cgggagtgcg ggcttcgggg atctctgctt     420
ggaactcaga ggcgctgacc cagcctgggg cccgtttgct gcccacggga ggagccgccg     480
tcagggctcg agatttctgt ggctcctcaa gatattggtc ataatcctgg tacttggcat     540
tgttggattt atgttcggaa gcatgttcct tcaagcagtg ttcagcagcc ccaagccaga     600
actcccaagt cctgccccgg gtgtccagaa gctgaagctt ctgcctgagg aacgtctcag     660
gaacctcttt tcctacgatg gaatctggtg agagactgcg tgttcttct ttcaccttaa      720
tgcacacatc ttccttgctc ctcctcaagt accatgccct actgtgccca ttgtaccgat     780
ggttcccttg ctttcctaag cctgtgctga atgcacaagt gactgcaagc caggatgggg     840
cttggtctgt acgatccagt ctatgttctc tatagcatcc agcaaaatcc cttaaaactt     900
tcgagagcat gtagttttt tttatcaaaa ctgcagaaaa gatgctgctt ctctgtctct      960
ctgccctcct tttatggtgg ggtgagatac aactgacagt cacgtggctc tcagatttaa     1020
agaagttagg tgcaggggac aattcaagag aggaaaagtc ttcagccttc ctctgtccct     1080
gcttccctcc ctttgtcccc ttgtctctgt gaggggccag tgcaagggac tccagggtct     1140
catcatctca gaacagttgg gtgtaggaaa gaagattttc agggtaaact acacactggt     1200
cctcttgctt gtttcaggct gttcccgaaa atcagtgca aatgtgaagc caacaaagag       1260
cagggaggtt acaactttca ggatgccatt ggccagagcg acctcccagc ggtgaaagcg     1320
aggagacagg ctgaatttga acactttcag aggaggtaat gcgggtcatg aaggcccttg     1380
```

-continued

| | | | | |
|---|---|---|---|---|
| ggttctgaga | tggaacaaaa | gccctccta | tgtcctgagg | ttgtgaatct taagagaaaa | 1440 |
| agcaggaagg | aattctctct | cttgcaaggg | tccctgggag | gaactattag gaatgaaaca | 1500 |
| aagaaggaat | cgaggaaatc | atccttaaat | gaagatttac | aaaactttgt atgtacaaaa | 1560 |
| catttcataa | caacaacaac | aacaacaaaa | agctgggatt | ggtgacacat gtctgtcatt | 1620 |
| ctagcacttt | gggaggtcaa | gatgggagga | tagcttgagc | ccaggagttt gagaccagct | 1680 |
| tgggcaatat | agtgagaccc | ccatcttcta | caaaacattt | ttaaaattag ccaggcatga | 1740 |
| tggtacatgc | ctgtagtccc | agctactcag | taggctgaag | tgagaggatc acttgagccc | 1800 |
| agaagttgaa | gctgcatgag | ccaggatcac | accactgcac | tccagcttga gaagggctgc | 1860 |
| cccgcccact | gccctgctg | gtccagccca | acctcccctt | tgggtaccca gtccacggag | 1920 |
| tggaggtgat | gccctgcac | acggttccca | tcccaggcct | ccagtttgaa ggacccgatg | 1980 |
| cccccgtcta | tgaggtcacc | ctgacagctt | ctctggggac | actgaacacc cttgctgatg | 2040 |
| tcccagacag | tgtggtgcag | ggcagaggcc | agaagcagct | gatcatttct accagtgacc | 2100 |
| ggaagctgtt | gaagttcatt | cttcagcacg | tgacatacac | cagcacgggg taccagcacc | 2160 |
| agaaggtaga | catagtgagt | ctggagtcca | ggtcctcagt | ggccaagttt ccagtgacca | 2220 |
| tccgccatcc | tgtcatacccc | aagctatacg | accctggacc | agagaggaag ctcagaaacc | 2280 |
| tggttaccat | tgctaccaag | actttcctcc | gccccacaa | gctcatgatc atgctccgga | 2340 |
| gtattcgaga | gtattaccca | gacttgaccg | taatagtggc | tgatgacagc cagaagcccc | 2400 |
| tggaaattaa | agacaaccac | gtggagtatt | acactatgcc | ctttgggaag ggttggtttg | 2460 |
| ctggtaggaa | cctggccata | tctcaggtca | ccaccaaata | cgttctctgg gtggacgatg | 2520 |
| attttctctt | caacgaggag | accaagattg | aggtgctggt | ggatgtcctg gagaaaacag | 2580 |
| aactggacgt | ggtaagggac | agttgccagt | ttcacccagc | cacaatctgt agagatggag | 2640 |
| aagagggag | aagagagcga | ggcggcagtg | tgctgggaaa | tgtgttccag tttaagttgt | 2700 |
| tgctggaaca | gagtgagaat | ggggcctgcc | ttcacaagag | gatgggattt ttccaacccc | 2760 |
| tggatggctt | cccagctgc | gtggtgacca | gtggcgtggt | caacttcttc ctggcccaca | 2820 |
| cggagcgact | ccaaagagtt | ggctttgatc | cccgcctgca | acgagtggct cactcagaat | 2880 |
| tcttcattga | tgggctaggg | accctactcg | tggggtcatg | cccagaagtg attataggtc | 2940 |
| accagtctcg | gtctccagtg | gtggactcag | aactggctgc | cctagagaag acctacaata | 3000 |
| cataccggtc | caacaccctc | acccgggtcc | agttcaagct | ggcccttcac tacttcaaga | 3060 |
| accatctcca | atgtgccgca | taaaggtgtg | agggcataga | gaaacactag gctggctggt | 3120 |
| atggtatcta | tagcagccac | caaaactgga | ctctgatagg | tgaacgttgt accaaccagc | 3180 |
| tgtggtaggg | aaaagggaaa | tggctcaagt | tactggaagt | accaatcaaa ggtgaagggt | 3240 |
| cact | | | | | 3244 |

HUMAN TRANSFERASE PROTEINS AND POLYNUCLEOTIDES ENCODING THE SAME

The present application claims the benefit of U.S. Provisional Application No. 60/170,408 which was filed on Dec. 13, 1999 and is herein incorporated by reference in its entirety.

1. INTRODUCTION

The present invention relates to the discovery, identification, and characterization of novel human polynucleotides encoding proteins sharing sequence similarity with mammalian glycotransferases. The invention encompasses the described polynucleotides, host cell expression systems, the encoded protein, fusion proteins, polypeptides and peptides, antibodies to the encoded proteins and peptides, and genetically engineered animals that either lack or over express the disclosed sequences, antagonists and agonists of the proteins, and other compounds that modulate the expression or activity of the proteins encoded by the disclosed polynucleotides that can be used for diagnosis, drug screening, clinical trial monitoring and the treatment of physiological disorders.

2. BACKGROUND OF THE INVENTION

Transferases covalently modify biological substrates, including protein, as part of degradation, maturation, and secretory pathways within the body. Transferases have thus been associated with, inter alia, development, protein and cellular senescence, and as cancer associated markers.

3. SUMMARY OF THE INVENTION

The present invention relates to the discovery, identification, and characterization of nucleotides that encode novel human proteins, and the corresponding amino acid sequences of these proteins. The novel human proteins (NHPS) described for the first time herein shares structural similarity with animal beta 1,4 N-acetylgalactosamine transferases.

The novel human nucleic acid (cDNA) sequences described herein, encode proteins/open reading frames (ORFs) of 506, 132, 72, 184, 124, 182, 118, 453, 393, 448, 388, 182, 122, 176, 116, 572, 512, and 566 amino acids in length (see SEQ ID NOS: 2, 4, 6, 8, 10, 12, 14, 16, 18, 20, 22, 24, 26, 28, 30, 32, 34, and 36).

The invention also encompasses agonists and antagonists of the described NHPs, including small molecules, large molecules, mutant NHPs, or portions thereof that compete with native NHPs, NHP peptides, and antibodies, as well as nucleotide sequences that can be used to inhibit the expression of the described NHPs (e.g., antisense and ribozyme molecules, and sequence or regulatory sequence replacement constructs) or to enhance the expression of the described NHPs (e.g., expression constructs that place the described sequence under the control of a strong promoter system), and transgenic animals that express a NHP transgene, or "knockouts" (which can be conditional) that do not express a functional NHP.

Further, the present invention also relates to processes for identifying compounds that modulate, i.e., act as agonists or antagonists, of NHP expression and/or NHP activity that utilize purified preparations of the described NHP and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequences of the NHP ORFs encoding the described NHP amino acid sequences. SEQ ID NO: 37 describes an ORF with flanking sequences.

5. DETAILED DESCRIPTION OF THE INVENTION

The NHPs, described for the first time herein, are novel proteins that are expressed in, inter alia, human cell lines, gene trapped cells and human kidney and stomach cells.

The described sequences were compiled from gene trapped cDNAs and clones isolated from a human kidney cDNA library (Edge Biosystems, Gaithersburg, Md.). The present invention encompasses the nucleotides presented in the Sequence Listing, host cells expressing such nucleotides, the expression products of such nucleotides, and: (a) nucleotides that encode mammalian homologs of the described sequences, including the specifically described NHPs, and the NHP products; (b) nucleotides that encode one or more portions of a NHP that correspond to functional domains of the NHP, and the polypeptide products specified by such nucleotide sequences, including but not limited to the novel regions of any active domain(s); (c) isolated nucleotides that encode mutant versions, engineered or naturally occurring, of a described NHP in which all or a part of at least one domain is deleted or altered, and the polypeptide products specified by such nucleotide sequences, including but not limited to soluble proteins and peptides in which all or a portion of the signal sequence is deleted; (d) nucleotides that encode chimeric fusion proteins containing all or a portion of a coding region of a NHP, or one of its domains (e.g., a receptor or ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing.

As discussed above, the present invention includes: (a) the human DNA sequences presented in the Sequence Listing (and vectors comprising the same) and additionally contemplates any nucleotide sequence encoding a contiguous NHP open reading frame (ORF), or a contiguous exon splice junction first described in the Sequence Listing, that hybridizes to a complement of a DNA sequence presented in the Sequence Listing under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of the DNA sequence that encode and express an amino acid sequence presented in the Sequence Listing under moderately stringent conditions, e.g., washing in 0.2×SSC/0.1% SDS at 42° C. (Ausubel et al., 1989, supra), yet still encode a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458). The invention also includes degenerate nucleic acid variants of the disclosed NHP polynucleotide sequences.

Additionally contemplated are polynucleotides encoding a NHP ORF, or its functional equivalent, encoded by a polynucleotide sequence that is about 99, 95, 90, or about 85 percent similar or identical to corresponding regions of the nucleotide sequences of the Sequence Listing (as measured by BLAST sequence comparison analysis using, for example, the GCG sequence analysis package using standard default settings).

The invention also includes nucleic acid molecules, preferably DNA molecules, that hybridize to, and are therefore the complements of, the described NHP nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing sequence expression patterns (particularly using a micro array or high-throughput "chip" format). Additionally, a series of the described NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS: 1–37 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS: 1–37, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the disclosures of which are herein incorporated by reference in their entirety.

Addressable arrays comprising sequences first disclosed in SEQ ID NOS:1–37 can be used to identify and characterize the temporal and tissue specific expression of a sequence. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–37.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ ID NOS:1–37 provides detailed information about transcriptional changes involved in a specific pathway, potentially leading to the identification of novel components or gene functions that manifest themselves as novel phenotypes.

Probes consisting of sequences first disclosed in SEQ ID NOS:1–37 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1–37 can be utilized in microarrays or other assay formats, to screen collections of genetic material from patients who have a particular medical condition. These investigations can also be carried out using the sequences first disclosed in SEQ ID NOS:1–37 in silico and by comparing previously collected genetic databases and the disclosed sequences using computer software known to those in the art.

Thus the sequences first disclosed in SEQ ID NOS:1–37 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS: 1–37. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relatve to one or more additional sequence(s) or one or more restriction sites present in the disclosed sequence.

For oligonucleotide probes, highly stringent conditions may refer, for example, to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP sequence antisense molecules, useful, for example, in NHP gene regulation (for and/or as antisense primers in amplification reactions of NHP nucleic acid sequences). With respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from human or non-human cell lines or tissue known or suspected to express an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP sequence, such as, for example, testis tissue). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP sequence can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, obesity, high blood pressure, connective tissue disorders, infertility, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue can be expressed and screened using standard antibody screening techniques in conjunction with antibodies raised against normal NHP product, as described below. (For screening techniques, see, for example, Harlow, E. and Lane, eds., 1988, "Antibodies: A Laboratory Manual", Cold Spring Harbor Press, Cold Spring Harbor).

Additionally, screening can be accomplished by screening with labeled NHP fusion proteins, such as, for example, alkaline phosphatase-NHP or NHP-alkaline phosphatase fusion proteins. In cases where a NHP mutation results in an expressed gene product with altered function (e.g., as a result of a missense or a frameshift mutation), polyclonal antibodies to NHP are likely to cross-react with a corresponding mutant NHP gene product. Library clones detected via their reaction with such labeled antibodies can be purified and subjected to sequence analysis according to methods well known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869, 336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP sequence under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the human cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of a NHP, as well as compounds or nucleotide constructs that inhibit expression of a NHP sequence (transcription factor inhibitors, antisense and ribozyme molecules, or gene or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of a NHP in the body. The use of engineered host cells and/or animals may offer an advantage in that such systems allow not only for the identification of compounds that bind to the endogenous receptor for a NHP, but can also identify compounds that trigger NHP-mediated activities or pathways.

Finally, the NHP products can be used as therapeutics. For example, soluble derivatives such as NHP peptides/domains corresponding to NHP, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP receptor. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHP, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The NHP Sequences

The cDNA sequences and the corresponding deduced amino acid sequences of the described NHP are presented in the Sequence Listing. SEQ ID NO:37 describes the NHP ORF as well as flanking regions. The NHP nucleotides were obtained from human cDNA libraries using probes and/or primers generated from human gene trapped sequence tags. Expression analysis has provided evidence that the described NHP can be expressed a variety of human cells as well as gene trapped human cells. A silent polymorphism (C-to-T transition) was identified at, for example, base 169 of SEQ ID NO:1.

5.2 NHP and NHP Polypeptides

NHPs, polypeptides, peptide fragments, mutated, truncated, or deleted forms of the NHPs, and/or NHP fusion proteins can be prepared for a variety of uses. These uses include, but are not limited to, the generation of antibodies, as reagents in diagnostic assays, for the identification of other cellular gene products related to a NHP, as reagents in assays for screening for compounds that can be as pharmaceutical reagents useful in the therapeutic treatment of mental, biological, or medical disorders and disease.

The Sequence Listing discloses the amino acid sequence encoded by the described NHP polynucleotides. The NHPs display initiator methionines in DNA sequence contexts consistent with translation initiation sites, and apparently display a signal sequence which can indicate that the described NHP ORFs are membrane associated or possibly secreted.

The NHP amino acid sequences of the invention include the amino acid sequences presented in the Sequence Listing as well as analogues and derivatives thereof, as well as any oligopeptide sequence of at least about 10–40, generally about 12–35, or about 16–30 amino acids in length first disclosed in the Sequence Listing. Further, corresponding NHP homologues from other species are encompassed by the invention. In fact, any NHP encoded by the NHP nucleotide sequences described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent gene product. Amino acid substitutions can be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where, as in the present instance, the NHP products or NHP polypeptides can be produced in soluble or secreted forms (by removing one or more transmembrane domains where applicable), the peptide or polypeptide can be recovered from the culture media. Such expression systems also encompass engineered host cells that express a NHP, or a functional equivalent, in situ. Purification or enrichment of NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays.

The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP encoding nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., OS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited, to the *E. coli* expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors (Pharmacia or American Type Culture Collection) can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign sequences. The virus grows in *Spodoptera frugiperda* cells.

A NHP coding sequence can be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted sequence is expressed (e.g., see Smith et al., 1983, J. Virol. 46:584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a nonessential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bittner et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in $tk^-$, $hgprt^-$ or $aprt^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the sequence of interest is subcloned into a vaccinia recombination plasmid such that the sequence's open reading frame is translationally fused to an amino-terminal tag consisting of six histidine residues. Extracts from cells infected with recombinant vaccinia virus are loaded onto $Ni^{2+}$•nitriloacetic acid-agarose columns and histidine-tagged proteins are selectively eluted with imidazole-containing buffers.

Also encompassed by the present invention are novel protein constructs engineered in such a way that they facilitate transport of the NHP to the target site, to the desired organ, across the cell membrane and/or to the nucleus where the NHP can exert its function activity. This goal may be achieved by coupling of the NHP to a cytokine or other ligand that would direct the NHP to the target organ and facilitate receptor mediated transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell. Alternatively targeting of NHP or its nucleic acid sequence might be achieved using liposome or lipid complex based delivery systems. Such technologies are described in *Liposomes:A Practical Approach,* New RRC ed., Oxford University Press, New York and in U.S. Pat. Nos. 4,594,595, 5,459,127, 5,948,767 and 6,110,490 and their respective disclosures which are herein incorporated by reference in their entirety.

5.3 Antibodies to NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP gene product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with the NHP, an NHP peptide (e.g., one corresponding to a functional domain of an NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, surface active substances such as lysolecithin, pluronic polyols, polyanions, peptides, oil emulsions, and potentially useful human adjuvants such as BCG (bacille Calmette-Guerin) and *Corynebacterium parvum.* Alternatively, the immune response could be enhanced by combination and or coupling with molecules such as keyhole limpet hemocyanin, tetanus toxoid, diptheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof.

The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the sequences from a mouse antibody molecule of appropriate antigen specificity together with sequences from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against NHP gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor can be used to generate anti-idiotypes that "mimic" the NHP and, therefore, bind and activate or neutralize a receptor. Such anti-idiotypic antibodies or Fab fragments of such anti-idiotypes can be used in therapeutic regimens involving a NHP signaling pathway.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. An isolated nucleic acid molecule having at least 85% identity with SEQ ID NO: 1, wherein said nucleic acid molecule encodes a protein having 1,4 N-acetylgalactosamine transferase activity.

2. An isolated nucleic acid molecule comprising a nucleotide sequence that:
    (a) encodes the amino acid sequence shown in SEQ ID NO: 2; and
    (b) hybridizes under stringent conditions to the nucleotide sequence of SEQ ID NO: 1 or the complement thereof, wherein the hybridization conditions are 0.5 M NaHPO$_4$, 7% sodium dodecyl sulfate (SDS), 1 mM EDTA at 65° C. followed by washing in 0.1×SSC/0.1% SDS at 68° C.

3. An isolated nucleic acid molecule encoding the amino acid sequence described in SEQ ID NO: 2.

4. A recombinant expression vector comprising a nucleic acid molecule of claim 3.

5. A host cell comprising the recombinant expression vector of claim 4.

* * * * *